United States Patent [19]

MacMillan

[11] Patent Number: 5,242,444
[45] Date of Patent: Sep. 7, 1993

[54] LUMBOSACRAL FIXATION AND FUSION METHOD AND DEVICE

[75] Inventor: Michael MacMillan, Gainesville, Fla.

[73] Assignee: University of Florida, Gainesville, Fla.

[21] Appl. No.: 787,537

[22] Filed: Nov. 4, 1991

[51] Int. Cl.⁵ ............................................. A61B 17/56
[52] U.S. Cl. .................................... 606/61; 606/60; 606/62; 606/79; 606/96
[58] Field of Search ............... 606/60, 61, 62, 79, 606/80, 96

[56] References Cited

U.S. PATENT DOCUMENTS

| 4,722,331 | 2/1988 | Fox | 606/96 |
| 4,739,751 | 4/1988 | Sapega et al. | 606/96 |
| 4,781,182 | 11/1988 | Purnell et al. | 606/96 |
| 4,883,048 | 11/1989 | Purnell et al. | 606/96 |
| 4,920,958 | 5/1990 | Walt et al. | 606/96 |
| 5,062,845 | 11/1991 | Kuslich et al. | 606/80 |

FOREIGN PATENT DOCUMENTS

| 350780 | 1/1990 | European Pat. Off. | 606/96 |
| 2747568 | 4/1979 | Fed. Rep. of Germany | 606/96 |

*Primary Examiner*—Robert A. Hafer
*Assistant Examiner*—Gregory M. Stone
*Attorney, Agent, or Firm*—Spensley Horn Jubas & Lubitz

[57] ABSTRACT

A method for percutaneously fixing and fusing the lumbosacral joint and a guide device for accurate placement of instrumentation to effect the fixation or fusion. The inventive method comprises placement of pins along bony canals leading bilateral of the spine from the pelvis to the S1 pedicles and then the vertebral body of L5.

8 Claims, 2 Drawing Sheets

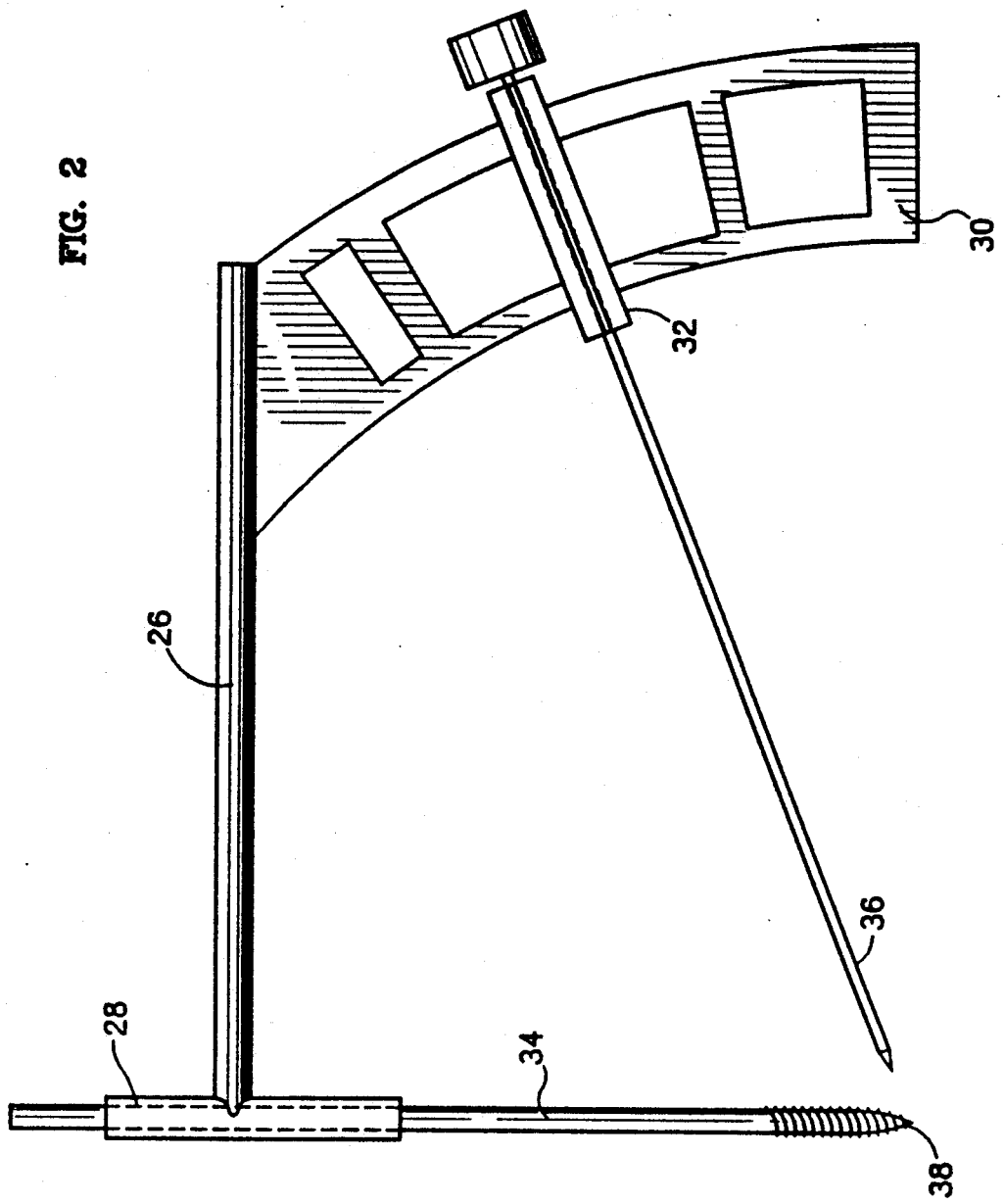

LUMBOSACRAL FIXATION AND FUSION METHOD AND DEVICE

BACKGROUND OF THE INVENTION

1. Field of the Invention

The present invention relates generally to spinal surgery involving the lower lumbar vertebrae. More specifically, the present invention relates to percutaneous lumbosacral fixation and fusion, and devices for performing these operations.

2. Related Art

It has been estimated that 70% of adults have had a significant episode of back pain. Millions of people suffer from the chronic lower back pain. Many of these people resort to surgical intervention to alleviate their pain. Approximately 95% of spinal surgery involves the lower lumbar vertebrae designated as the fourth lumbar vertebra ("L4"), the fifth lumbar vertebra ("L5"), and the first sacral vertebra ("S1").

Persistent low back pain is attributed primarily to degeneration of the disc connecting L5 and S1. There are two possible mechanisms whereby intervertebral disc lesions can instigate and propagate low back pain. The first theory proposes that the intervertebral disc itself trauma or degeneration and becomes the primary source of low back pain. Proponents of this theory advocate removal of the painful disc to relieve the low back pain. Two extensive procedures are available to remove the disc and fuse the adjacent vertebrae together. One method is to replace the disc with bone plugs by going through the spinal canal on either side of the central nerve bundle. This method requires extensive stripping of the paraspinal musculature. More importantly, there are extensive surgical manipulations within the spinal canal itself. Although the initial proponents of this approach report 90% excellent to good results, subsequent studies have been unable to obtain acceptable outcomes and recommend adding internal fixation to improve fusion rates.

The second procedure is the anterior lumbar fusion which avoids the morbidity of posterior muscle stripping by approaching the spine through the abdomen. Surgeons experienced with this technique also report good to excellent patient results in 90% of cases performed. However, when generally used by practicing surgeons, the procedure was found to have a high failure rate of fusion. Attempts to increase the fusion rate by performing a posterior stabilization procedure have been successful, but the second incision increases the morbidity and decreases the advantages of the technique. Thus, the present surgical techniques available to remove and fuse painful lumbar discs are extensive operative procedures with potentially significant complications.

The other proposed mechanism for the intervertebral disc to cause low back pain concerns its affect on associated supportive tissues. The theory states that disc narrowing leads to stress on all of the intervertebral structures. These include the vertebral bodies, ligamentous supports, and facet joints. Surgeries designed to fuse and stabilize the intervertebral segment can be performed through the posterior approach. This is the original surgical procedure which was used to treat low back pain. This approach again entails extensive muscular stripping and bone preparation.

There is, therefore, no single procedure which is universally accepted to surgically manage low back pain patients. Although with sophisticated diagnostic imaging deranged discs can be identified, the surgical procedures are so extensive that clinical outcomes are not consistently satisfactory. Furthermore, patients undergoing presently available fusion surgery experience uncomfortable, prolonged convalescence.

Presently available surgical fixation and fusion techniques involving the lower lumbar vertebrae thus suffer from numerous disadvantages. The present invention has the objective of overcoming such disadvantages.

SUMMARY OF THE INVENTION

The present invention provides a method and device for percutaneous fixation and fusion of the lumbosacral vertebrae. Specifically, the present invention comprises the placement of instrumentation through the S1 pedicle to the vertebral body of L5 on both sides of the spine. The present invention further provides a method for percutaneous removal of the L5-S1 disc and for bone graft placement.

The inventor has discovered that a bony pathway leads from the pelvis directly to the body of the S1 vertebra and then to the body of the L5 vertebra on each side of the spine. The present invention exploits this discovery by providing a method for fusing or fixing the lumbosacral joint by placing instrumentation such as screws through the discovered bony pathways. The invention further provides a device to guide placement of the instrumentation percutaneously using known radiographic techniques.

The inventive guide device may be connected to a localizing instrument, e.g., a pin anchored in the S1 pedicle. Once the device is connected to the localizing instrument, the shape of the device permits localization of the bony pathway leading to the vertebral body of L5. Details of the inventive method and device will become clear upon review of the drawing and the following detailed description.

BRIEF DESCRIPTION OF THE DRAWINGS

FIG. 2 is a side view of the inventive guide.

Like reference numbers in the drawings refer to like elements.

DETAILED DESCRIPTION OF THE INVENTION

Figure 1:
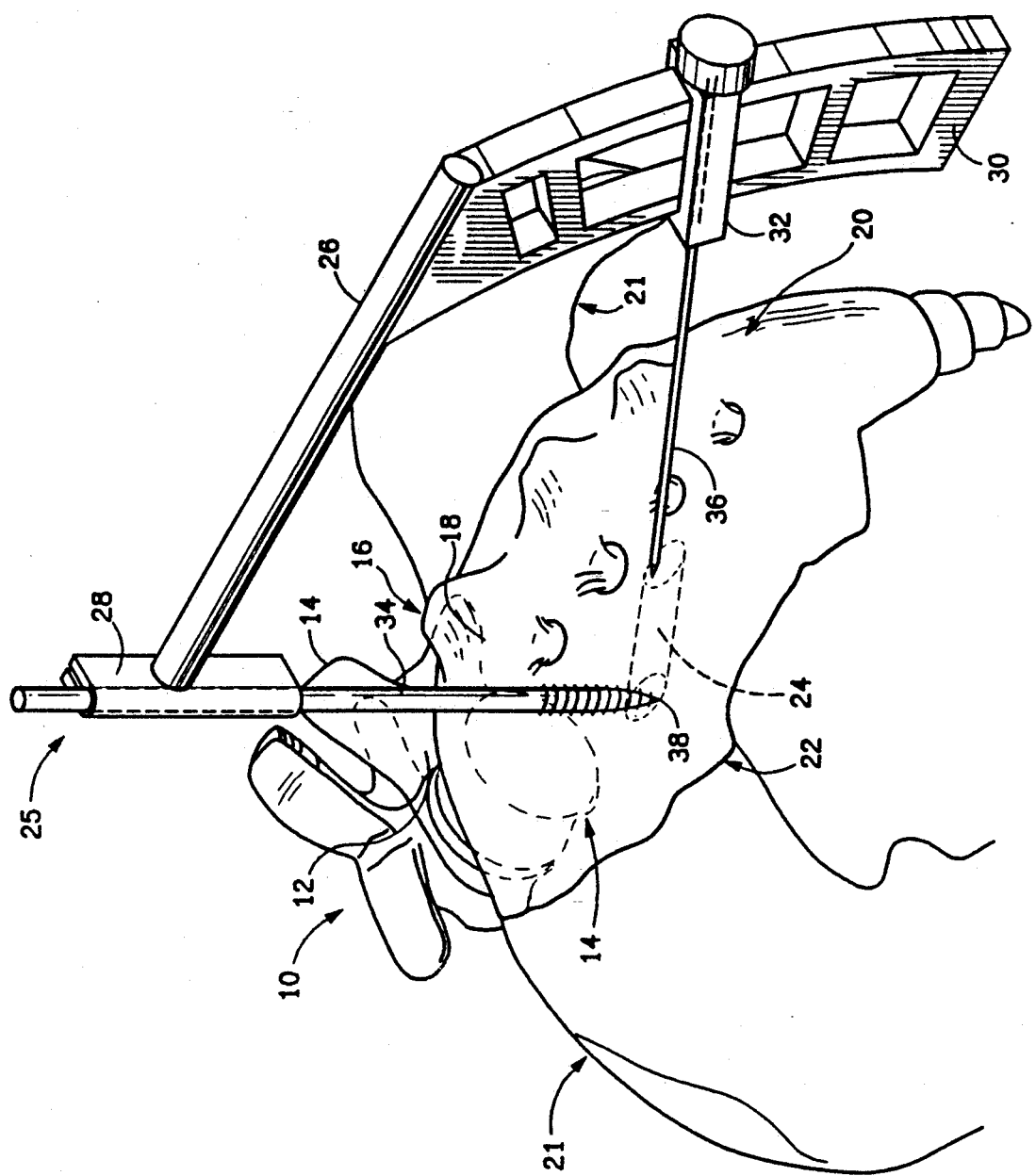
FIG. 1 is a perspective view of a segment of the human spine showing the inventive device properly positioned to effect fixation of the lumbosacral joint.

The following description is of the best presently contemplated mode of carrying out the invention. This description is made for the purpose of illustrating the general principles of the invention and should not be taken in a limiting sense. The scope of the invention is best determined by reference to the appended claims.

The inventor has determined that a bony pathway on each side of the spine, leading from the iliac crest of the pelvis directly through the pedicle of the first sacral vertebra ("S1") and then to the vertebral body of the fifth lumbar vertebra ("L5") on each side of the spine, provides an optimum pathway for placement of surgical instrumentation to effect fixation and fusion of the lumbosacral joint. The inventive method comprises fixation and fusion of the lumbosacral joint utilizing these bony pathways.

FIG. 1 shows the bony structures of the relevant portion of a human spine 10 including the fifth lumbar vertebra L5 12 with its vertebral body 14, the first sacral vertebra S1 16 including the S1 pedicle 18, the iliac crest area 20 of the pelvis 21, the sacral endplate 22, and one of the bony pathways 24 originating at the ilac crest 20, proceeding through one of the S2 pedicles 18, and entering the L5 vertebral body 14.

Studies performed by the inventor have disclosed that three radiographic landmarks describe each of the bony pathways 24. These three landmarks are (1) the neuroforamen from which the small skin nerves arise which supply the hip area; (2) the S1 pedicle 18; and (3) the bottom portion of the iliac crest 20 near the sacral iliac joint. The first step of the inventive method involves isolating these landmarks using standard radiographic technique so as to identify the bony pathway 24 in a particular patient.

In the preferred embodiment of the inventive method, the patient's trunk, head and arms are positioned to rest on an operating table. The patient's knees are preferably bent at a 90° angle and held in padded cups which extend 24–30 inches from the end of the operating table. A fluoroscope is positioned under the abdomen so as to arc around the torso, thereby permitting lateral views of the relevant sections of the spine. Pre-operative fluoroscopy of the lower spine and sacrum is then performed to locate the three radiographic landmarks which describe one bony pathway 24.

Next, the patient's skin of the spine overlying S1 pedicles 18 is marked and a stab wound is made through the skin over S1 pedicle 18. Under fluoroscopic control, localizing instrumentation (e.g., a pin or K-wire) 34 provided with a pre-selected depth restriction (e.g., a shoulder) is then percutaneously placed through the stab wound into the center of the S1 pedicle 18 to penetrate into the adjacent bony pathway 24. The pedicle localizing instrumentation 34 is placed parallel to the sacral endplate 22. The depth of penetration of the instrumentation to reach the bony pathway 24 (i.e., the length of the localizing pin below the shoulder) is determined from preoperative radiographic studies of the patient's spine. Proper positioning of the instrumentation is confirmed fluoroscopically.

FIGS. 1 and 2 depict a preferred embodiment of the inventive guide device 25 used for accurate placement of surgical instrumentation within the bony pathways 24. The guide 25 preferably includes a first, linear member 26 having a length ranging from 7 to 10 inches, preferably approximately 8 inches, which is typically sufficient to span the lower spine of a typical adult. The first member 26 is provided with a first bracket 28 mounted at approximately a 90° angle at or near its distal end for receiving an S1 pedicle localizing instrumentation 34. A second, curved member 30 having a fixed radius of curvature of about 20 degrees is connected to the proximal end of the first member 26. The curved member 30 is provided with a second bracket 32 for receiving a penetration instrument 36. The second bracket 32 may be moved along the length of the curved member 30 and fixed in position at any point along the length thereof.

While the first member 26 of the preferred embodiment is described as linear and depicted in FIG. 1 as a straight rod and the second member 30 is described and depicted as being curved, other configurations may be utilized. For example, the curved member 30 may be replaced by a linear member provided with a bracket having a curved track of the required radius of curvature. Alternatively, the two members 26, 30 may be replaced by a single curved member, resembling a bow, and provided with a stationary bracket at its distal end for receiving the S1 pedicle localizing instrumentation 34 and a movable bracket which may travel along its proximal end for directing the instrumentation into the bony pathway 24.

The length of the first member 26 and the radius of curvature of the second member 30 are selected such that the longitudinal axis of the penetration instrument 36 intercepts the penetrating end 38 of the pedicle localizing instrumentation 34 regardless of the position of bracket 32 along the length of the curved member 30. Thus, the guide device 25 compensates for normal anatomical differences of the human spine. In the illustrated embodiment, if the length of the first member 26 is about 8 inches, then the radius of curvature for the second member 30 should be about 20°. All of the materials used in the inventice device should be sterilizable and relatively rigid. Medical-grade stainless steel or titanium is preferred for all components. In the preferred embodiment of the inventive method, the posterior inferior iliac crest 20 is palpated bilaterally of the spine and the overlying skin is marked. Next, a stab wound is made over each of these bony prominences. Under fluoroscopic guidance, an entry point is placed into the bone using, for example, a bone awl. The inventive guide device 25 is then positioned by attaching the first bracket 28 to the pedicle localizing instrumentation 34 previously positioned into the pedicle of S1. The guide device 25 is positioned so that the curved member 30 is placed adjacent the iliac crest area 20 of the spine. Under radiographic guidance, the second bracket 32 is then positioned along the curved member 30 so that the penetration instrument 36 placed into the bracket 32 enters the bony pathway 24 from the posterior iliac crest area 20 and meets the penetrating end 38 of the pedicle localizing instrument 34 positioned in the S1 pedicle 18.

Next, the penetration instrument 36 may then be advanced through the S1 pedicle 18 along the bony pathway 24, across the S1-L5 disk, and into the L5 vertebral body 14. Once the penetration instrument 36 has been placed, the pedicle localizing instrumentation 34 may be withdrawn from the S1 pedicle 18 and the guide device 25 may be removed. The penetration instrument 36 thus placed may be utilized to introduce a cannulated drill to widen the pathway for placement of a screw for fixation of the lumbosacral joint or for insertion of a suction-cutter arthroscopic tool to actually break up and remove the L5-S1 disc material if desired. Additionally, cannulated tools may be inserted over the penetration instrument 36 to, for example, introduce osteogenic material between S1 and L5 to allow actual percutaneous spinal fusion.

The skill needed to properly apply the inventive guide device 25 to the pelvis is limited to the localization of the S1 pedicle 18, a standard surgical spinal technique already widely in use for the placement of screws. Thus, use of the inventive device and guide does not require retaining of the orthopedic surgeon.

An embodiment of the present invention could be used in conjunction with computed tomography for more precise placement of the localization instrument. Furthermore, the invention could also be applied to diseases of the sacroiliac joint. Traumatic disruptions of this joint could be fixated by utilizing the instrumentation to place screws across the joint.

One preferred embodiment of the present inventive method and the inventive device has been illustrated and described. Nevertheless, it will be understood that various modifications may be made without departing from the spirit and scope of the invention. For example, the inventive method includes placement of the penetration instrument 36 through a bony pathway 24 freehand, i.e., without a guide device 25; or the method may utilize other devices for placing the penetration instrument 36. As previously mentioned, the first and second members 26, 30 of the inventive guide device may be replaced by a solitary curved member or by two members of different configurations. Additionally, the inventive guide may be made of other materials, e.g., plastic. Accordingly, it is to be understood that the invention is not to be limited by the specific illustrated embodiment, but only by the scope of the appended claims.

I claim:

1. A method for percutaneously fixing or fusing the lumbosacral joint of a patient comprising the step of placing bone penetration instrumentation bilateral of the spine through the pedicles of S1 across the S1-L5 disk into the vertebral body of L5.

2. The method of claim 1 wherein the penetration instrumentation is placed along at least one of the two bony pathways existing on the sides of the spine leading from the iliac crest through the S1 pedicle to the vertebral body of L5.

3. The method of claim 2 further comprising the step of locating at least one such bony pathway pre-operatively using fluoroscopic studies of the patient's spine and pelvis.

4. The method of claim 3 further comprising the steps of:
    (a) percutaneously placing a pedicle localizing instrument having a penetration end into at least one pedicle of S1 to mark the location of at least one associated bony pathway;
    (b) attaching a guide device to each pedicle localizing instrument placed in an S1 pedicle, the guide device further having means for accurately directing a bone penetration instrument into the associated bony pathway;
    (c) introducing a bone penetration instrument into the bony pathway with the guide device;
    (d) detaching the guide device from the pedicle localizing instrument.

5. The method of claim 4 wherein the guide device includes a first member provided with a bracket at or near its distal end for receiving the pedicle localizing instrument, and a second member attached to the proximal end of the first member and having a bracket movable along its length for receiving a penetration instrument, the second member being curved such that the longitudinal axis of a received penetration instrument intercepts the penetration end of the pedicle localizing instrument placed in the S1 pedicle.

6. A guide device for introducing surgical instrumentation into at least one bony pathway leading from the iliac crest of the pelvis to the pedicle of the S1 vertebra and from there to the vertebral body of the L5 vertebra, comprising:
    (a) a first linear member having a length ranging from 8 to 10 inches and having a bracket at or near its distal end for attaching a pedicle localizing instrument having a penetration end, the bracket being mounted at an approximately 90° angle to the first member; and
    (b) a second member connected to the proximal end of the first member and having a bracket for receiving a penetration instrument, the bracket being movable in a curve with respect to the second member such that the longitudinal axis of a received penetration instrument intercepts the penetration end of the pedicle localizing instrument.

7. The guide of claim 6, wherein the rate of curvature of the second member is 20°.

8. A method for percutaneously removing the L5-S1 disc of a patient comprising the steps of:
    (a) drilling a hole along at least one of the two bony pathways existing on the sides of the spine leading from the iliac crest through the S1 pedicle to the vertebral body of L5;
    (b) inserting a suction-cutter arthroscopic tool into the hole;
    (c) breaking up the L5-S1 disc material; and
    (d) removing the L5-S1 disc material.

* * * * *